US011324176B1

(12) United States Patent
Danziger et al.

(10) Patent No.: US 11,324,176 B1
(45) Date of Patent: May 10, 2022

(54) ***IMPATIENS HAWKERI* PLANTS 'NGT-15-5000', 'NGT-17-7039', 'NGT-18-7090', AND 'NGT-18-3080'**

(71) Applicant: Danziger 'DAN' Flower Farm, Beit Dagan (IL)

(72) Inventors: Gavriel Danziger, Beit Dagan (IL); Pnina Amir, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

(21) Appl. No.: 17/085,307

(22) Filed: Oct. 30, 2020

(51) Int. Cl.
  *A01H 6/16* (2018.01)
  *A01H 5/10* (2018.01)
(52) U.S. Cl.
  CPC ............... *A01H 6/165* (2018.05); *A01H 5/10* (2013.01)
(58) Field of Classification Search
  CPC .................................................. A01H 6/165
  See application file for complete search history.

(56) References Cited

U.S. PATENT DOCUMENTS

PP30,855 P3 * 8/2019 Lee ..................... A01H 5/02
                                                       Plt./318.2

* cited by examiner

*Primary Examiner* — David H Kruse
(74) *Attorney, Agent, or Firm* — Cassandra Bright

(57) ABSTRACT

The invention relates to the field of *Impatiens hawkeri*, in particular, varieties designated 'NGT-15-5000', 'NGT-17-7039', 'NGT-18-7090', and 'NGT-18-3080' including the plants and seeds thereof. The present invention relates to plants parts, including cells and any propagative material of the new varieties 'NGT-15-5000', 'NGT-17-7039', 'NGT-18-7090', and 'NGT-18-3080', and use of any of the plant parts for reproducing the new varieties 'NGT-15-5000', 'NGT-17-7039', 'NGT-18-7090', and 'NGT-18-3080'. The present invention relates to methods using any plant parts of 'NGT-15-5000', 'NGT-17-7039', 'NGT-18-7090', and/or 'NGT-18-3080' for the purpose of deriving new *Impatiens* varieties. The present invention relates to seed, plants and plant parts produced by crossing 'NGT-15-5000', 'NGT-17-7039', 'NGT-18-7090', and 'NGT-18-3080' with any other *Impatiens* variety.

9 Claims, 8 Drawing Sheets

(7 of 8 Drawing Sheet(s) Filed in Color)

IMPATIENS HAWKERI PLANTS 'NGT-15-5000', 'NGT-17-7039', 'NGT-18-7090', AND 'NGT-18-3080'

FIELD OF THE INVENTION

The present invention relates to new varieties of *Impatiens hawkeri*, hereinafter referred it as 'NGT-15-5000', 'NGT-17-7039', 'NGT-18-7090', and 'NGT-18-3080', sharing a new, distinct and stable characteristic of reduced apical dominance. The present invention relates to seeds which are the *Impatiens hawkeri* 'NGT-15-5000', 'NGT-17-7039', 'NGT-18-7090', and 'NGT-18-3080', as well as, plants and the plant parts produced by these seeds which have all the morphological and physiological characteristics of *Impatiens hawkeri* 'NGT-15-5000', 'NGT-17-7039', 'NGT-18-7090', and 'NGT-18-3080'. The present invention also relates to methods for producing these seeds and plants of the *Impatiens hawkeri* 'NGT-15-5000', 'NGT-17-7039', 'NGT-18-7090', and 'NGT-18-3080'. Furthermore, the present invention relates to a method of producing progeny *Impatiens* plants by crossing any of the varieties *Impatiens* 'NGT-15-5000', 'NGT-17-7039', 'NGT-18-7090', and 'NGT-18-3080', as either the female or seed or male or pollen parent, with another *Impatiens* plant and selecting progeny.

BACKGROUND OF THE INVENTION

The present invention relates to new, distinct and stable varieties of *Impatiens hawkeri*, and hereinafter referred to by the variety denomination 'NGT-15-5000', 'NGT-17-7039', 'NGT-18-7090', and 'NGT-18-3080'. The new *Impatiens* 'NGT-15-5000', 'NGT-17-7039', 'NGT-18-7090', and 'NGT-18-3080' originated from a controlled breeding program begun during 2001 in Israel. The new varieties were selected between 2015 and 2018.

During 2001 a naturally occurring whole plant mutation of a proprietary *I. hawkeri* variety was identified and selected for its interesting plant morphology. The breeding program resulting in these new varieties of *Impatiens hawkeri* was developed from this initial selection.

The initial progeny selected from the breeding presented the following characters: low growth, axillary bud emergence very close to the ground, short internodes, small leaves and small flowers, compact flat structure, the diameter of the plant was up to 15 cm and its height did not exceed 10 cm. The 4 varieties described herein all exhibit the axillary bud emergence low on the main stem recognized in parental generations. Further breeding was conducted within the proprietary population to intensify and stabilize this characteristic.

Concurrently a breeding program was developed to introduce these desirable characteristics into *I. hawkeri* plants having large flowers, attractive foliage in a range of commercially important flower colors.

Progeny were selected which exhibited the unique reduced apical dominance trait combined with other esthetically commercial traits. A selection was made of four varieties consistently exhibiting the phenotypic reduced apical dominance, as well as highly similar plant morphology.

*Impatiens* belong to the family Balsaminacea and is a Genus consisting of 850 to 900 species which are native to Eurasia and Africa. *Impatiens* are fleshy Extensive breeding programs exist for *Impatiens*. Methods for propagation are well known and include seed, vegetative cuttings and tissue culture.

*Impatiens hawkeri* is one of the most important species of commercial flowering bedding plants. Ornamental breeders seek to improve upon known characteristics as well as develop new and useful features.

When grown in pots for ornamental horticulture, an important characteristic of New Guinea *Impatiens* is a tendency for some self-branching (Martin, 1984; Kaczperski, 1989). The branching forms an attractive ornamental flowering potted product. These pots usually contain 1 to 3 cuttings of the propagative material in order to maximize ornamental value. It is of interest to commercial growers to cultivate varieties with greater branching to make fuller, more ornamental pots with the least quantity of cuttings and labor input. It is the objective of the breeder to fulfill this need with new and improved varieties.

The market is full of New Guinea *Impatiens*(NGI) plants with very little variation in morphology. NGI have great color range in flowers and in foliage. However, the regular known structure and shape of the *Impatiens hawkeri* plant is less than optimal for hanging baskets, terrace gardens, container gardens. Any planting criteria requiring a plant with a well-branched base is not well-served by current varieties.

Known commercial varieties of *Impatiens hawkeri* have a dominant central stem, resulting in weak to moderate lateral branching. In most varieties the main stem remains significantly dominant throughout the development of the plant. Additionally, the location of the first node on the main stem in most of the known varieties will be relatively high on the stem, and the axillary buds will be fairly dormant. This is typically a result of apical dominance. The formation of the shoots from the axillary buds on the first node occurs very late in the development, when the apical meristem has elongated significantly from the base of the plant.

The formation of basal or very low emerging branches results in a plant which is very full and attractively well-branched. Known varieties which begin branching higher on the stem grow more vertically and take longer to make a full, attractive plant. The low and basal branching quality has significant potential to reduced propagative inputs for growers.

Objectives of breeding programs are defined by the problems and weaknesses of the current cultivars. Interspecific crosses have been made to improve branching characteristics in *Impatiens hawkeri*. The varieties described herein are pure *Impatiens hawkeri* plants, having improved branching without the introduction of another species. Plants retain the desirable *I. hawkeri* traits of attractive foliage and large flowers, together with novel improved branching.

As pure *Impatiens hawkeri* plants, the new varieties are differentiated from the prior art, U.S. Pat. No. 6,924,416. The subject of U.S. Pat. No. 6,924,416 is a trailing, interspecific *Impatiens*. In addition to other differences obvious to those trained in the art, the improvements described herein involved *Impatiens hawkeri* plants having semi-trailing habits.

SUMMARY OF THE INVENTION

The following embodiments and aspects thereof are described in conjunction with systems, tools and methods which are meant to be exemplary, not limiting in scope.

The present invention provides *Impatiens hawkeri* plant selections exhibiting reduced apical dominance, increased development of axillary buds, and emergence of axillary buds in a low position on the stem. Additionally, plants of 'NGT-15-5000', 'NGT-17-7039', 'NGT-18-7090', and 'NGT-18-3080' typically produce many side shoots, with these side shoots starting to emerge at a lower section of the main stem than typical of *Impatiens*. Plants begin flowering uniquely early. These qualities, combined with the descriptions included herein, distinguish the new cultivars from known *Impatiens hawkeri* varieties.

These and other objectives have been achieved in accordance with the present invention which provide 'NGT-15-5000', 'NGT-17-7039', 'NGT-18-7090', and 'NGT-18-3080' as new *Impatiens* cultivars that were products of a planned breeding program conducted by the inventor in Moshav Mishmar Hashiva, Israel.

The new varieties 'NGT-15-5000', 'NGT-17-7039', 'NGT-18-7090', and 'NGT-18-3080' can be produced by sexual or asexual reproduction to produce a population of progeny plants, each of which has the combination of characteristics as herein disclosed for the new varieties 'NGT-15-5000', 'NGT-17-7039', 'NGT-18-7090', and 'NGT-18-3080'.

Deposit Information 625 seeds which are the variety 'NGT-15-5000' have been deposited with the National Collection of Industrial Food and Marine Bacteria (NCIMB), Ferguson Building, Bucksburn, Aberdeen, Scotland, a Budapest Treaty recognized depository which affords permanence of the deposit, and accorded International Depository Authority Accession No. NCIMB-43657. 625 seeds which are the variety 'NGT-17-7039' have been deposited with the NCIMB, accorded Accession No. NCIMB-43739. 625 seeds which are the variety 'NGT-18-7090' have been deposited with NCIMB and accorded Accession No. NCIMB 43708. 625 seeds which are the variety 'NGT-18-3080' have been deposited with the NCIMB and accorded Accession No. 43709.

BRIEF DESCRIPTION OF THE DRAWINGS

The patent or application file contains multiple drawings executed in color. Copies of this patent or patent application publication with color drawing will be provided by the Office upon request and payment of the necessary fees.

The accompanying photographs illustrate the unique growth habit and overall appearance of the new *Impatiens hawkeri* 'NGT-15-5000', 'NGT-17-7039', 'NGT-18-7090', and 'NGT-18-3080' showing the colors as true as is reasonably possible with colored reproductions of this type. Colors in the photograph may differ slightly from the color values cited in the detailed botanical description which accurately describes the color of 'NGT-15-5000', 'NGT-17-7039', 'NGT-18-7090', and 'NGT-18-3080'.

OBJECTS OF THE INVENTION

Figure 1:
FIG. 1 illustrates a top view of plants of *Impatiens hawkeri* 'NGT-15-5000', 'NGT-17-7039', 'NGT-18-7090', and 'NGT-18-3080' at 34 days of age. This photo was taken Jan. 28, 2020 in Moshav Mishmar Hashiva, Israel.
Figure 1:
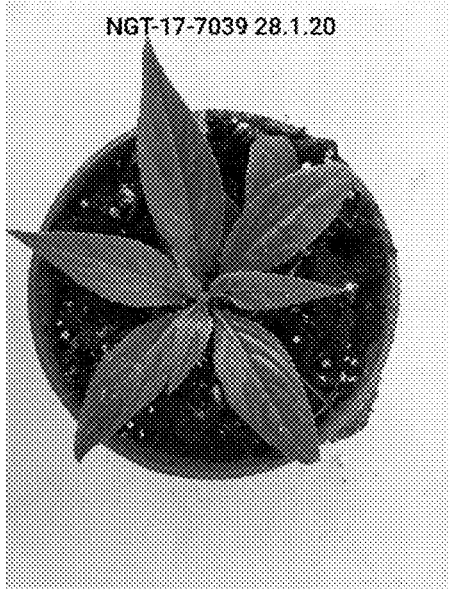
Figure 1:
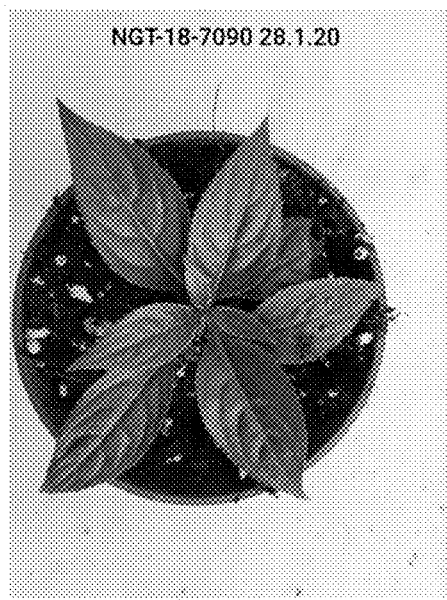
Figure 1:
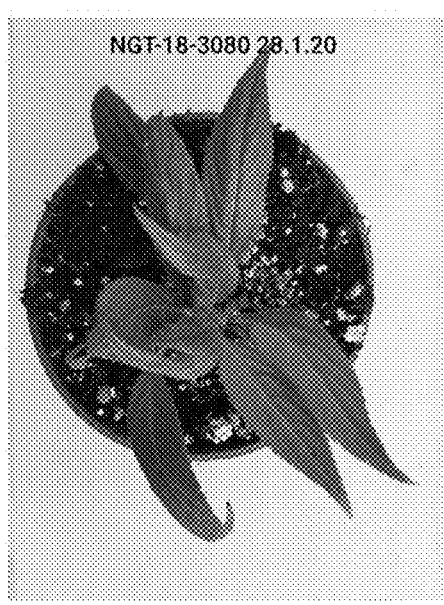
Figure 2:
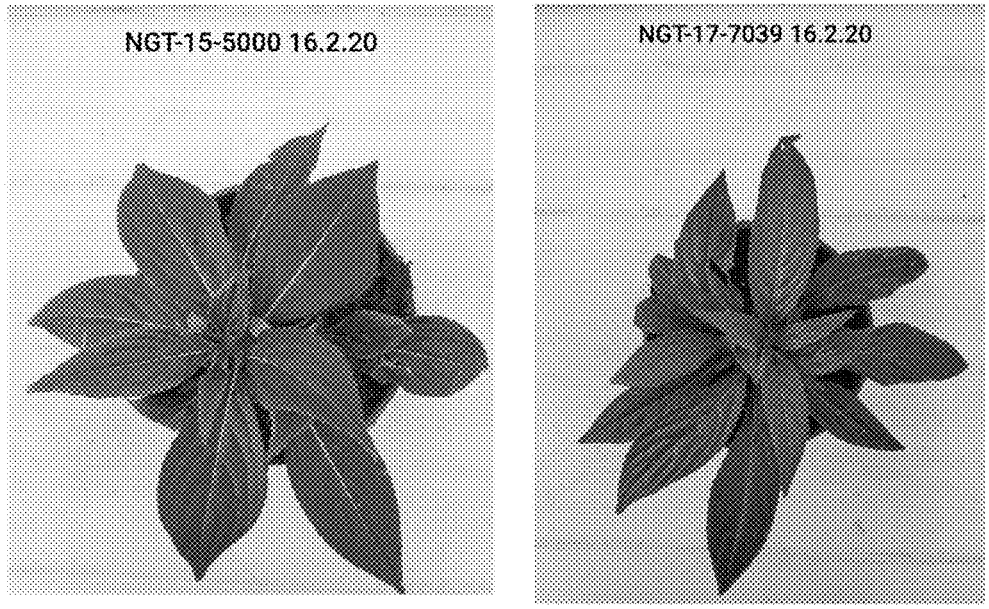
FIG. 2 illustrates a top view of the same plants of *Impatiens hawkeri* 'NGT-15-5000', 'NGT-17-7039', 'NGT-18-7090', and 'NGT-18-3080' at 53 days of age. This photo was taken Feb. 16, 2020 in Moshav Mishmar Hashiva, Israel.
Figure 2:
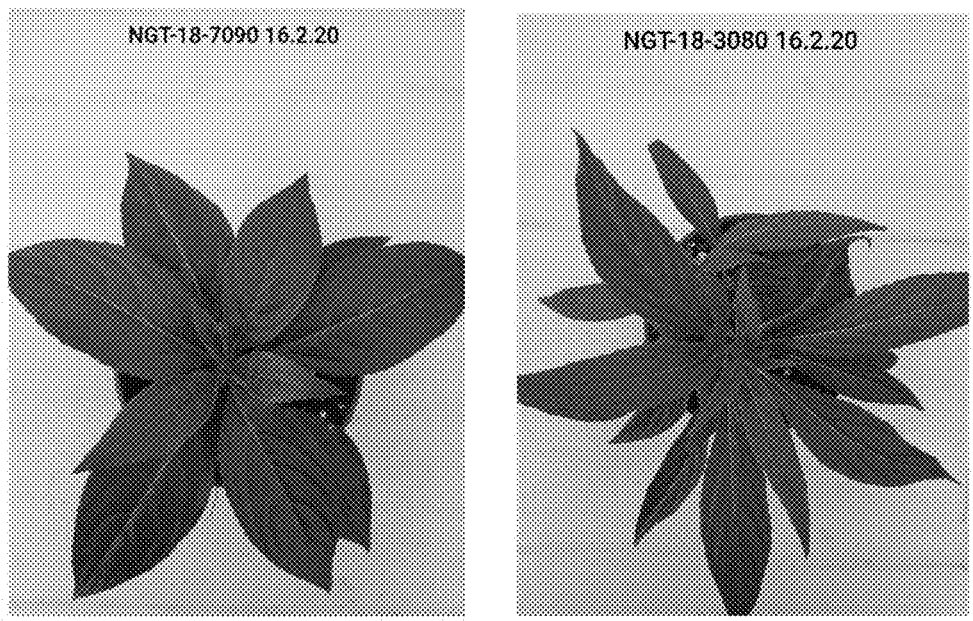
Figure 3:
FIG. 3 illustrates a side view of *Impatiens hawkeri* 'NGT-17-7039', with typical low emerging and abundant axillary growth.
Figure 4:
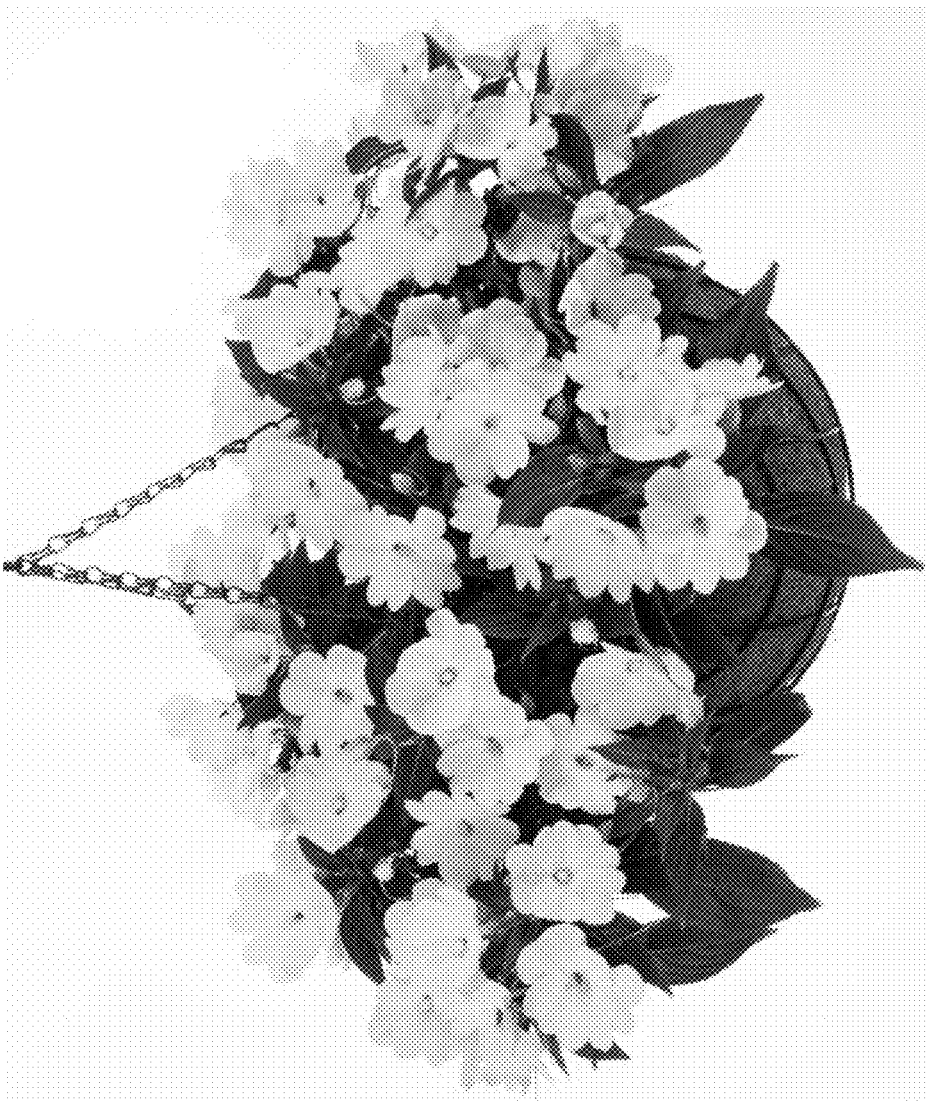
FIG. 4. illustrates a flowering plant of 'NGT-15-5000'.
Figure 5:
FIG. 5. illustrates a flowering plant of 'NGT-17-7039'.
Figure 6:
FIG. 6. illustrates a flowering plant of 'NGT-18-3080'.
Figure 7:
FIG. 7. illustrates a flowering plant of 'NGT-1-7090'.
Figure 8:
FIG. 8 illustrates a close up view of flowers of *Impatiens hawkeri* 'NGT-15-5000', 'NGT-17-7039', 'NGT-18-7090', and 'NGT-18-3080'
Figure 8:
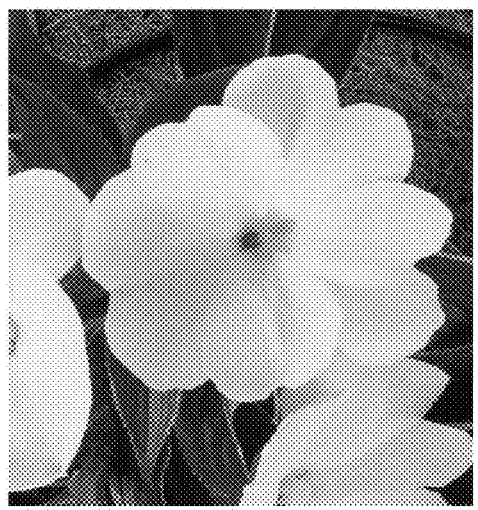
Figure 8:
Figure 8:

The following embodiments and aspects thereof are described in conjunction with system, tools and methods which are meant to be exemplary, not limiting in scope The present invention relates to *Impatiens* plants, and parts thereof, having all the physiological and morphological characteristics of *Impatiens hawkeri* 'NGT-15-5000', 'NGT-17-7039', 'NGT-18-7090', and 'NGT-18-3080'.

Another embodiment relates to seeds which produce *Impatiens hawkeri* 'NGT-15-5000', 'NGT-17-7039', 'NGT-18-7090', and 'NGT-18-3080'.

Another embodiment relates to a plant produced from seeds which are *Impatiens hawkeri* 'NGT-15-5000', 'NGT-17-7039', 'NGT-18-7090', and/or 'NGT-18-3080'.

Another embodiment relates to a plant produced by vegetative means which are *Impatiens hawkeri* 'NGT-15-5000', 'NGT-17-7039', 'NGT-18-7090', and/or 'NGT-18-3080'. The present invention also relates to plant parts, such as pollen, seeds or inflorescence produced by *Impatiens hawkeri* 'NGT-15-5000', 'NGT-17-7039', 'NGT-18-7090', and 'NGT-18-3080'.

Another embodiment relates to a method of producing seed which are *Impatiens hawkeri* 'NGT-15-5000', 'NGT-17-7039', 'NGT-18-7090', and 'NGT-18-3080'.

Another embodiment also relates to a method of producing plants having all the physiological and morphological characteristics of the *Impatiens hawkeri* 'NGT-15-5000', 'NGT-17-7039', 'NGT-18-7090', and 'NGT-18-3080' comprising the steps of (a) self-pollinating *Impatiens hawkeri* 'NGT-15-5000', 'NGT-17-7039', 'NGT-18-7090', and/or 'NGT-18-3080' a (b) harvesting seeds produced from said cross; and (c) producing plants from said harvested seeds.

The present invention also relates to producing progeny plants from the cross of *Impatiens hawkeri* 'NGT-15-5000', 'NGT-17-7039', 'NGT-18-7090', and/or 'NGT-18-3080', as the female or male parent, with another *Impatiens* plant, and selecting progeny plants from this cross.

The present invention also relates to producing progeny plants of *Impatiens hawkeri* 'NGT-15-5000', 'NGT-17-7039', 'NGT-18-7090', and/or 'NGT-18-3080', by any known means of vegetative propagation.

The present invention also relates to producing progeny plants of *Impatiens hawkeri* 'NGT-15-5000', 'NGT-17-7039', 'NGT-18-7090', and/or 'NGT-18-3080', from natural or induced mutation.

Another embodiment relates to tissue culture produced from protoplast of cells form the New *Impatiens* plants disclosed in the subject application, wherein said cells or protoplasts are produced from a plant part selected from the group consisting of pollen, ovules, embryos, protoplasts, meristematic cells, callus, leaves, anthers, cotyledons, hypcotyl, pistils, roots, root tips, flowers, seeds, petiole and stems.

Another embodiment relates to a plant or a part thereof, produced by growing *Impatiens hawkeri* 'NGT-15-5000', 'NGT-17-7039', 'NGT-18-7090', and/or 'NGT-18-3080', wherein the plant part comprises at least one cell of *Impatiens hawkeri* 'NGT-15-5000', 'NGT-17-7039', 'NGT-18-7090', and/or 'NGT-18-3080'.

Another embodiment relates to tissue or cell culture of regenerable cells produced from the plants of *Impatiens hawkeri* 'NGT-15-5000', 'NGT-17-7039', 'NGT-18-7090', and/or 'NGT-18-3080'. And an *Impatiens hawkeri* plant regenerated from the tissue or cell culture of *Impatiens hawkeri* 'NGT-15-5000', 'NGT-17-7039', 'NGT-18-7090', and/or 'NGT-18-3080'.

Another embodiment relates to a method of vegetatively propagating the plant of *Impatiens hawkeri* 'NGT-15-5000', 'NGT-17-7039', 'NGT-18-7090', and/or 'NGT-18-3080', comprising the steps of: collecting tissue or cells capable of being propagated from a plant of *Impatiens hawkeri* 'NGT-15-5000', 'NGT-17-7039', 'NGT-18-7090', and/or 'NGT-18-3080'; cultivating said tissue or cells to obtain proliferated shoots; and rooted said shoots to obtain rooted plantlets; or cultivating said tissue or cells to obtain shoots or to obtain plantlets and a plant produced by growing the plantlets or shoots of said plant.

A further embodiment relates to a method for developing an *Impatiens hawkeri* plant in an *Impatiens hawkeri* breeding program, comprising applying plant breeding technique comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to the *Impatiens* plant of *Impatiens hawkeri* 'NGT-15-5000', 'NGT-17-7039', 'NGT-18-7090', and/or 'NGT-18-3080', or its parts, wherein application of said techniques results in development of an *Impatiens hawkeri* plant.

A further embodiment relates to a method of introducing a mutation into the genome of *Impatiens hawkeri* 'NGT-15-5000', 'NGT-17-7039', 'NGT-18-7090', and/or 'NGT-18-3080', and wherein the resulting plant comprises at least one genome mutation and producing plants there from.

In addition to the exemplary aspects and embodiments described above, further aspects and embodiments will become apparent by study of the following descriptions.

Detailed Botanical Description

The present invention was developed by the inventor, in Moshav Mishmar Hashiva, Israel.

This invention is directed to *Impatiens hawkeri* plants having all the morphological and physiological characteristics of the variety 'NGT-15-5000', 'NGT-17-7039', 'NGT-18-7090', and 'NGT-18-3080' produced from either vegetative terminal cuttings, or seed.

The new *Impatiens hawkeri* 'NGT-15-5000', 'NGT-17-7039', 'NGT-18-7090', and 'NGT-18-3080' can also be produced by asexually reproducing progeny. Asexual reproduction of the new cultivar by vegetative means was first performed by leaf cuttings during May of 2018, in Moshav Mishmar Hashiva, Israel. The first 'NGT-15-5000', 'NGT-17-7039', 'NGT-18-7090', and 'NGT-18-3080' plants propagated through the use of such cuttings are maintained in Moshav Mishmar Hashiva, Israel and have reproduced at least 5 generations. Subsequent asexual reproduction has demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'NGT-15-5000', 'NGT-17-7039', 'NGT-18-7090', and 'NGT-18-3080' which in combination distinguish these *Impatiens* as new and distinct cultivars:

1. Reduced apical dominance resulting in increased axillary bud development.
2. Emergence of axillary growth low on the stem.
3. Semi-trailing plant habit.
4. Large flowers.

The new *Impatiens hawkeri* 'NGT-15-5000' can be compared to the unpatented *Impatiens hawkeri* 'Harmony White'. Plants of 'Harmony White' differ from plants of 'NGT-15-5000' in the following:

1. 'NGT-15-5000' has a semi-trailing growth habit, with more branches than this comparator, which has a mounding growth habit.
2. 'NGT-15-5000', has a smaller flower than this comparator.
3. 'NGT-15-5000' has narrower foliage than this comparator.

*Impatiens hawkeri* 'NGT-15-5000' can also be compared to the unpatented *Impatiens hawkeri* 'Harmony Snow'. Plants of 'Harmony Snow' differ from plants of 'NGT-15-5000' in the following:

1. 'NGT-15-5000' has a semi-trailing growth habit, with more branches than this comparator, which has a mounding growth habit.
2. 'NGT-15-5000', has a smaller flower than this comparator.
3. 'NGT-15-5000' has narrower foliage than this comparator.
4.

*Impatiens hawkeri* 'NGT-15-5000' can also be compared to *Impatiens hawkeri* 'IMGZ0010', USPP 30,855. Plants of 'IMGZ0010' differ from plants of 'NGT-15-5000' in the following:

1. 'NGT-15-5000' has a semi-trailing growth habit, this comparator, which has a compact growth habit, as described in USPP 30,855.
2. 'NGT-15-5000' has longer branches than this comparator, producing plants having a width of approximately 60 cm; width of this comparator is described as 20 cm in USPP 30,855.
3. 'NGT-15-5000' produces more main branches lateral branches than this comparator, on average 15, compared to 6.

The new *Impatiens hawkeri* 'NGT-17-7039' can be compared to the unpatented *Impatiens hawkeri* 'Harmony Perfect Pink'. Plants of 'Harmony Perfect Pink' differ from plants of 'NGT-17-7039' in the following:

1. 'NGT-17-7039' has a semi-trailing growth habit, with more branches than this comparator, which has a mounding growth habit.
2. 'NGT-17-7039' has narrower foliage than this comparator.
3. Flower color of 'NGT-17-7039' *is* a different shade of pink than this comparator.

The new *Impatiens hawkeri* 'NGT-17-7039' can also be compared to the unpatented *Impatiens hawkeri* 'Harmony Blush'. Plants of 'Harmony Blush' differ from plants of 'NGT-17-7039' in the following:

1. 'NGT-17-7039' has a semi-trailing growth habit, with more branches than this comparator, which has a mounding growth habit.
2. 'NGT-17-7039' has narrower foliage than this comparator.
3. Flower color of 'NGT-17-7039' *is* a different shade of pink than this comparator.

The new *Impatiens hawkeri* 'NGT-18-7090' can also be compared to the unpatented *Impatiens hawkeri* 'Harmony Perfect Pink'. Plants of 'Harmony Perfect Pink' differ from plants of 'NGT-18-7090' in the following:
1. 'NGT-18-7090' has a semi-trailing growth habit, with more branches than this comparator, which has a mounding growth habit.
2. 'NGT-18-7090' has smaller flowers than this comparator.
3. Flower color of 'NGT-17-7039' is a much darker shade than this comparator.

The new *Impatiens hawkeri* 'NGT-18-7090' can also be compared to the unpatented *Impatiens hawkeri* 'Harmony Red Cardinal'. Plants of 'Harmony Red Cardinal' differ from plants of 'NGT-18-7090' in the following:
1. 'NGT-18-7090' has a semi-trailing growth habit, with more branches than this comparator, which has a mounding growth habit.
2. 'NGT-18-7090' has darker foliage than this comparator.
3. Flower color of 'NGT-18-7090' is a much darker shade than this comparator.

The new *Impatiens hawkeri* 'NGT-18-3080' can be compared to the unpatented *Impatiens hawkeri* 'Harmony Perfect Pink'. Plants of 'Harmony Perfect Pink' differ from plants of 'NGT-18-3080' in the following:
1. 'NGT-18-3080' has a semi-trailing growth habit, with more branches than this comparator, which has a mounding growth habit.
2. 'NGT-18-3080' has narrower foliage than this comparator.
3. Flower color of 'NGT-18-3080' a different shade of pink than this comparator.

The new *Impatiens hawkeri* 'NGT-18-3080' can also be compared to the unpatented *Impatiens hawkeri* 'Harmony Pastel Lavender'. Plants of 'Harmony Pastel Lavender' differ from plants of 'NGT-18-3080' in the following:
1. 'NGT-18-3080' has a semi-trailing growth habit, with more branches than this comparator, which has a mounding growth habit.
2. 'NGT-18-3080' has narrower foliage than this comparator.
3. Flower color of 'NGT-18-3080' is pink, flower color of this comparator is lavender.
4. Flower size of 'NGT-18-3080' is smaller than this comparator.

'NGT-15-5000', 'NGT-17-7039', 'NGT-18-7090', and 'NGT-18-3080' have not been tested and observed under all possible environmental conditions. The phenotype of the new cultivars may vary with variations in environment such as temperature, light intensity, frequency of fertilization, composition of fertilizer, flowering treatment, day length and humidity, without any change in the genotype of the plant.

For example, substantial differences in plant height and diameter; depending upon environmental conditions and planting density.

The aforementioned drawings, together with the following observations, measurements and values describe the new *Impatiens* 'NGT-15-5000', 'NGT-17-7039', 'NGT-18-7090', and 'NGT-18-3080' as grown in a greenhouse in Moshav Mishmar Hashiva, Israel. Plants of 'NGT-15-5000', 'NGT-17-7039', 'NGT-18-7090', and 'NGT-18-3080' were grown in a research greenhouse with temperatures ranging from approximately 5° C. to 18° C. during the day and night temperatures ranging from approximately 20° C. to 30° C. in the day and approximately 15° C. to 25° C. in the day. No artificial lighting or photoperiodic treatments were conducted. Plants were measured at approximately 6 months old from a rooted cutting.

Color reference are made to the Royal Horticultural Society Colour Chart (RHS), 2001 edition, except where general colors of ordinary significance are used. Color values were taken under daylight conditions in a greenhouse in Moshav Mishmar Hashiva, Israel.

The information below lists additional botanical characteristics of *Impatiens hawkeri* 'NG-T-15-5000'

PLANT:

| | |
|---|---|
| Growth Habit: | Semi-Trailing |
| Height: | About 20 to 30 cm. |
| Plant Spread: | About 60 cm |
| Growth Rate: | Medium. |
| Branching Characteristics: | Very well branched. |
| Length of Primary Lateral Branches: | 25 cm. |
| Quantity of Primary Lateral Branches: | 15. |
| Characteristics of Primary Lateral Branches: | |
| Form: | Round. |
| Diameter: | 5 mm |
| Color: | RHS Yellow-Green 146C. |
| Texture: | Smooth. |
| Strength: | Strong, very stable. |
| Internode length: | 2-3 cm. |

FOLIAGE

| | |
|---|---|
| Leaf: | |
| Arrangement: | Alternate. |
| Quantity: | Approximately 15-20 per branch. |
| Average Length: | 7.5 cm. |
| Average Width: | 2.5 cm. |
| Shape of blade: | Lanceolate. |
| Apex: | Attenuate. |
| Base: | Acuminate. |
| Margin: | Ciliate. |
| Texture of surfaces: | Smooth. |
| Pubescence: | None. |
| Aspect: | 45°. |
| Color: | |
| Young foliage upper side: | RHS Green 137B. |
| Young foliage under side: | RHS Yellow-Green 146C. |
| Mature foliage upper side: | RHS Yellow-Green 147A. |
| Mature foliage under side: | RHS Yellow-Green 147C. |
| Venation: | |
| Type: | Midrib with secondary veins. Pinnate, only lower surface. |
| Venation color upper side: | Midrib RHS Yellow-Green 145B. |
| Venation color under side: | RHS Yellow-Green 147C. |
| Petiole: | |
| Length: | 1.5 cm. |
| Diameter: | 0.2 cm. |
| Color: | RHS Yellow-Green 145D. |
| Texture: | Smooth. |

FLOWER

| | |
|---|---|
| Natural flowering season: | Flowers at any day length. All year round in a greenhouse environment. Flowering is continuous from spring until fall in an outdoor garden. |

| FLOWER | |
|---|---|
| Days to flowering from rooted cutting: | 9-10 weeks. |
| Inflorescence and flower type and habit: | Single flowers raised above the foliage. The corolla consists of five petals. |
| Rate of flower opening: | 10 to 15 days from bud to fully opened flower. |
| Flower Longevity on Plant: | 5-7 days. |
| Bud: | |
| Shape: | Ovate. |
| Length: | 1.5 cm. |
| Diameter: | 1 cm. |
| Color: | RHS Green-Yellow 1D. |
| Flower size: | |
| Diameter: | 7.0 cm. |
| Depth: | 0.3 cm. |
| Petals: | |
| Quantity: | 5. |
| Arrangement: | Overlapping whorl. |
| Length: | 3 cm. |
| Width: | 3 cm. |
| Shape: | Round. |
| Apex: | Heart-shape. |
| Base: | Acute. |
| Margin: | Entire. |
| Texture, upper and lower surfaces: | Smooth. |
| Color: | |
| When opening, upper surface: | RHS White N155B. |
| When opening, lower surface: | RHS White NN155D. |
| Fully opened, upper surface: | RHS White N155B. |
| Spurs: | |
| Quantity per flower: | 1. |
| Length: | 6 cm. |
| Diameter: | 0.1 cm. |
| Aspect: | Spur curvature 40°-45° from peduncle. |
| Color: | RHS Yellow-Green 149D. |
| Apex: | RHS Yellow-Green 145A. |
| Sepals: | |
| Quantity: | 2. |
| Length: | 1 cm. |
| Width: | 0.5 cm. |
| Shape (overall): | Oblong. |
| Apex: | Acute. |
| Base: | Rounded. |
| Margin: | Entire. |
| Color: | RHS Yellow-Green 145C. |
| Peduncles: | |
| Length: | 4 cm. |
| Diameter: | 0.1 cm. |
| Angle: | About 45° to the lateral branch. |
| Strength: | Stable, flexible. |
| Texture: | Smooth. |
| Color: | RHS Yellow-Green 144D. |
| Fragrance: | None. |

| REPRODUCTIVE ORGANS | |
|---|---|
| Stamens: | |
| Number: | There are five stamens with introrse anthers that are more or less fused and form a cap over the ovary. |
| Anthers: | |
| Shape: | Oblong. |
| Length: | Approximately 0.5 cm. |
| Color: | RHS White NN155B. |
| Pollen: | |
| Color: | RHS White 155A. |
| Quantity: | Abundant. |
| Pistil: | |
| Number: | 1. |
| Length: | 0.5 cm. |
| Style: | |
| Length: | 0.3 cm. |
| Color: | RHS Yellow-Green 144D. |
| Stigma: | |
| Shape: | Round. |
| Color: | RHS Green-White 157A. |
| Ovary Color: | RHS Yellow-Green N144C. |

Other Characteristics

Seeds and fruits: 10 to 20 seeds per fruit.
The information below lists additional botanical characteristics of *Impatiens hawkeri*

'NGT-17-7039'

Plant
Growth Habit: Semi trailing.
Pot size of plant described: 20 cm.
Height: 20 cm.
Plant Spread: 60 cm.
Growth Rate: Medium.
Branching Characteristics: Highly branched.
Length of Primary Lateral Branches: 25 cm.
Quantity of Primary Lateral Branches: 30.
Characteristics of Primary Lateral Branches:
    Form: Rounded shape.
    Diameter: 0.5 cm.
    Color: RHS Yellow-Green 146D.
    Texture: Smooth.
    Strength: Strong, very stable.
Internode length: 6-7 cm.

| FOLIAGE | |
|---|---|
| Leaf: | |
| Arrangement: | Alternate. |
| Quantity: | Approximately 15-20 per branch. |
| Average Length: | 9 cm. |
| Average Width: | 2.5 cm. |
| Shape of blade: | Lanceolate. |
| Apex: | Attenuate. |
| Base: | Acuminate. |
| Margin: | Ciliate. |
| Texture of surfaces: | Smooth. |
| Pubescence: | None. |
| Aspect: | 45°. |
| Color: | |
| Young foliage upper side: | RHS Yellow-Green 146A. |
| Young foliage under side: | RHS Yellow-Green 146C. |
| Mature foliage upper side: | RHS Yellow-Green 147A. |
| Mature foliage under side: | RHS Yellow-Green 147C. |
| Venation: | |
| Type: | Midrib with secondary veins. Pinnate, only lower surface. |

-continued

| FOLIAGE | |
|---|---|
| Venation color upper side: | Midrib RHS Yellow-Green 145C. |
| Venation color under side: | RHS Yellow-Green 146B |
| Petiole: | |
| Length: | 2 cm. |
| Diameter: | 0.2 cm. |
| Color: | RHS Greyed-Red 181D. |
| Texture: | Smooth. |

| FLOWER | |
|---|---|
| Natural flowering season: | Flowers at any day length. All year round in a greenhouse environment. Flowering is continuous from spring until fall in an outdoor garden. |
| Days to flowering from rooted cutting: | 9-10 weeks. |
| Inflorescence and flower type and habit: | Single flowers raised above the foliage. The corolla consists of five petals. |
| Rate of flower opening: | 10 to 15 days from bud to fully opened flower. |
| Flower Longevity on Plant: | 5-7 days. |
| Persistent or Self-Cleaning: | Yes. |
| Bud: | |
| Shape: | Ovate. |
| Length: | 2 cm. |
| Diameter: | 1 cm. |
| Color: | RHS Red-Purple 69A. |
| Flower size: | |
| Diameter: | 7.5 cm. |
| Depth: | 0.2 cm. |
| Petals: | |
| Quantity: | 5. |
| Arrangement: | Overlapping. |
| Length: | 3.5 cm. |
| Width: | 5 cm. |
| Shape: | Round. |
| Apex: | Heart-shape. |
| Base: | Acute. |
| Margin: | Entire. |
| Texture, upper and lower surfaces: | Smooth. |
| Color: | |
| When opening, upper surface: | RHS Red-Purple 68D and Red 41A. |
| When opening, lower surface: | RHS Red-Purple 68D. |
| Fully opened, upper surface: | RHS Red-Purple 65C and Red 41B. |
| Spurs: | |
| Quantity per flower: | 1. |
| Length: | 6.5 cm. |
| Diameter: | 0.1 cm. |
| Aspect: | Spur curvature 40° to 45° from peduncle. |
| Color: | RHS Red 47A. |
| Apex: | RHS Yellow-Green 146D. |
| Sepals: | |
| Quantity: | 2. |
| Length: | 1.5 cm. |
| Width: | 0.5 cm. |
| Shape (overall): | Oblong. |
| Apex: | Acute. |
| Base: | Rounded. |
| Margin: | Entire. |
| Color: | RHS Yellow-Green 145B. |
| Peduncles: | |
| Length: | 3.5-4 cm. |
| Diameter: | 0.1 cm. |

-continued

| FLOWER | |
|---|---|
| Angle: | About 45° to the lateral branch. |
| Strength: | Stable, flexible. |
| Texture: | Smooth. |
| Color: | RHS Greyed-Orange 177D. |
| Fragrance: | None. |

| REPRODUCTIVE ORGANS | |
|---|---|
| Stamens: | |
| Number: | There are five stamens with introrse anthers that are more or less fused and form a cap over the ovary. |
| Anthers: | |
| Shape: | Oblong. |
| Length: | Approximately 0.2 cm. |
| Color: | RHS White 155A. |
| Pollen: | |
| Color: | RHS White group 155D. |
| Quantity: | Abundant. |
| Pistil: | |
| Number: | 1. |
| Length: | 0.5 cm. |
| Style: | |
| Length: | 0.4 cm. |
| Color: | RHS Yellow-Green 144B. |
| Stigma: | |
| Shape: | Round. |
| Color: | RHS Green-White 155B. |
| Ovary Color: | RHS Yellow-Green N144D. |

Other Characteristics

Seeds and fruits: 10 to 20 seeds per fruit.

The information below lists additional botanical characteristics of *Impatiens hawkeri*

'NGT-18-7090'

Plant

Growth Habit: Semi trailing.

Pot size of plant described: 20 cm.

Height: 20 to 30 cm.

Plant Spread: 60 to 70 cm.

Growth Rate: Medium.

Branching Characteristics: Highly branched.

Length of Primary Lateral Branches: 35 cm.

Quantity of Primary Lateral Branches: 40.

Characteristics of Primary Lateral Branches:

Form: Rounded shape.

Diameter: 0.5 cm.

Color: RHS Yellow-Green 146C.

Texture: Smooth.

Strength: Strong, very stable.

Internode length: 5-6 cm.

FOLIAGE

Leaf:

| | |
|---|---|
| Arrangement: | Alternate. |
| Quantity: | Approximately 20-25 per branch. |
| Average Length: | 8.5 cm. |
| Average Width: | 2.5 cm. |
| Shape of blade: | Lanceolate. |
| Apex: | Attenuate. |
| Base: | Acuminate. |
| Margin: | Ciliate. |
| Texture of top surface: | Smooth. |
| Pubescence: | None. |
| Aspect: | 45°. |
| Color: | |
| Young foliage upper side: | RHS Yellow-Green 144A. |
| Young foliage under side: | RHS Yellow-Green 146C. |
| Mature foliage upper side: | RHS Yellow-Green 146A. |
| Mature foliage under side: | RHS Yellow-Green 143C. |
| Venation: | |
| Type: | Midrib with secondary veins. Pinnate, only lower surface. |
| Venation color upper side: | Midrib RHS Greyed-Red 181D. |
| Venation color under side: | RHS Green 137C. |
| Petiole: | |
| Length: | 1.5 cm. |
| Diameter: | 0.2 cm. |
| Color: | RHS Greyed-Red 182D. |
| Texture: | Smooth. |

FLOWER

| | |
|---|---|
| Natural flowering season: | Flowers at any day length. All year round in a greenhouse environment. Flowering is continuous from spring until fall in an outdoor garden. |
| Days to flowering from rooted cutting: | 9-10 weeks. |
| Inflorescence and flower type and habit: | Single flowers raised above the foliage. The corolla consists of five petals. |
| Rate of flower opening: | 10 to 15 days from bud to fully opened flower. |
| Flower Longevity on Plant: | 5-7 days. |
| Bud: | |
| Shape: | Ovate. |
| Length: | 2 cm. |
| Diameter: | 1 cm. |
| Color: | RHS Red-Purple N66A. |
| Flower size: | |
| Diameter: | 7 cm. |
| Depth: | 0.3 cm. |
| Petals: | |
| Quantity: | 5. |
| Arrangement: | Overlapping. |
| Length: | 4 cm. |
| Width: | 4 cm. |
| Shape: | Round. |
| Apex: | Heart-shape. |
| Base: | Acute. |
| Margin: | Entire. |
| Texture, upper and lower surfaces: | Smooth. |
| Color: | |
| When opening, upper surface: | RHS Red 45B. |
| When opening, lower surface: | RHS Red 43A. |
| Fully opened, upper surface: | RHS Red 45B. |

FLOWER -continued

| | |
|---|---|
| Spurs: | |
| Quantity per flower: | 1. |
| Length: | 6.5 cm. |
| Diameter: | 0.1 cm. |
| Aspect: | Spur curvature 40°-45° from peduncle. |
| Color: | RHS Red 47A. |
| Apex: | RHS Yellow-Green 144B. |
| Sepals: | |
| Quantity: | 2. |
| Length: | 1.5 cm. |
| Width: | 0.5 cm. |
| Shape (overall): | Oblong. |
| Apex: | Acute. |
| Base: | Rounded. |
| Margin: | Entire. |
| Color: | RHS Yellow-Green 145C. |
| Peduncles: | |
| Length: | 4 cm. |
| Diameter: | 0.1 cm. |
| Angle: | About 45° to the lateral branch. |
| Strength: | Stable, flexible. |
| Texture: | Smooth. |
| Color: | RHS Yellow-Green 145D. |
| Fragrance: | None. |

REPRODUCTIVE ORGANS

| | |
|---|---|
| Stamens: | |
| Number: | There are five stamens with introrse anthers that are more or less fused and form a cap over the ovary. |
| Anthers: | |
| Shape: | Oblong. |
| Length: | Approximately 0.5 cm. |
| Color: | RHS White N155D. |
| Pollen: | |
| Color: | RHS White group 155D. |
| Quantity: | Abundant. |
| Pistil: | |
| Number: | 1. |
| Length: | 0.5 cm. |
| Style: | |
| Length: | 0.4 cm. |
| Color: | RHS Yellow-Green 145C. |
| Stigma: | |
| Shape: | Round. |
| Color: | RHS Yellow-Green 145C. |
| Ovary Color: | RHS Yellow-Green 145C. |

Other Characteristics

Seeds and fruits: 10 to 15 seeds per fruit.
The information below lists additional botanical characteristics of *Impatiens hawkeri*

'NGT-18-3080'

Plant
Growth Habit: Semi trailing.
Pot size of plant described: 20 cm.
Height: 20 to 30 cm.
Plant Spread: 60 cm.
Growth Rate: Medium.

Branching Characteristics: Highly branched.
Length of Primary Lateral Branches: 30 cm.
Quantity of Primary Lateral Branches: 50.
Characteristics of Primary Lateral Branches:
    Form: Rounded shape.
    Diameter: 0.5 cm.
    Color: RHS Yellow-Green 145A.
    Texture: Smooth.
    Strength: Strong, very stable.
Internode length: 5-6 cm.

| FOLIAGE | |
|---|---|
| Leaf: | |
| Arrangement: | Alternate. |
| Quantity: | Approximately 20-25 per branch. |
| Average Length: | 8.5 cm. |
| Average Width: | 2.3 cm. |
| Shape of blade: | Lanceolate. |
| Apex: | Attenuate. |
| Base: | Acuminate. |
| Margin: | Ciliate. |
| Texture of top surface: | Smooth. |
| Pubescence: | None. |
| Aspect: | 45°. |
| Color: | |
| Young foliage upper side: | RHS Yellow-Green 144A. |
| Young foliage under side: | RHS Yellow-Green 145B. |
| Mature foliage upper side: | RHS Green N137B. |
| Mature foliage under side: | RHS Green N138B. |
| Venation: | |
| Type: | Midrib with secondary veins. Pinnate, only lower surface. |
| Venation color upper side: | Midrib RHS Yellow-Green 145B. |
| Venation color under side: | RHS Yellow-Green 147C. |
| Petiole: | |
| Length: | 2 cm. |
| Diameter: | 0.2 cm. |
| Color: | RHS Yellow-Green 147D. |
| Texture: | Smooth. |

| FLOWER | |
|---|---|
| Natural flowering season: | Flowers at any day length. All year round in a greenhouse environment. Flowering is continuous from spring until fall in an outdoor garden. |
| Days to flowering from rooted cutting: | 9-10 weeks. |
| Inflorescence and flower type and habit: | Single flowers raised above the foliage. The corolla consists of five petals. |
| Rate of flower opening: | 10 to 15 days from bud to fully opened flower. |
| Flower Longevity on Plant: | 5-7 days. |
| Bud: | |
| Shape: | Ovate. |
| Length: | 2 cm. |
| Diameter: | 1 cm. |
| Color: | RHS Purple 75A. |
| Flower size: | |
| Diameter: | 6.5 cm. |
| Depth: | 0.3 cm. |
| Petals: | |
| Quantity: | 5. |
| Arrangement: | Overlapping whorl. |
| Length: | 4 cm. |
| Width: | 4 cm. |
| Shape: | Round. |

| FLOWER | |
|---|---|
| Apex: | Heart-shape. |
| Base: | Acute. |
| Margin: | Entire. |
| Texture, upper and lower surfaces: | Smooth. |
| Color: | |
| When opening, upper surface: | RHS Red-Purple N74C. |
| When opening, lower surface: | RHS Purple 75B. |
| Fully opened, upper surface: | RHS Red-Purple N74C. |
| Spurs: | |
| Quantity per flower: | 1. |
| Length: | 7 cm. |
| Diameter: | 0.1 cm. |
| Aspect: | Spur curvature 40°-45° from peduncle. |
| Color: | RHS Yellow-Green 145D. |
| Apex: | RHS Yellow-Green 145A. |
| Sepals: | |
| Quantity: | 2. |
| Length: | 1 cm. |
| Width: | 0.5 cm. |
| Shape (overall): | Oblong. |
| Apex: | Acute. |
| Base: | Rounded. |
| Margin: | Entire. |
| Color: | RHS Yellow-Green 145C. |
| Peduncles: | |
| Length: | 4 cm. |
| Diameter: | 0.1 cm. |
| Angle: | About 45° to the lateral branch. |
| Strength: | Stable, flexible. |
| Texture: | Smooth. |
| Color: | RHS Yellow-Green 145B. |
| Fragrance: | None. |

| REPRODUCTIVE ORGANS | |
|---|---|
| Stamens: | |
| Number: | There are five stamens with introrse anthers that are more or less fused and form a cap over the ovary. |
| Anthers: | |
| Shape: | Oblong. |
| Length: | Approximately 0.5 cm. |
| Color: | RHS White N155D. |
| Pollen: | |
| Color: | RHS White 155D. |
| Quantity: | Abundant. |
| Pistil: | |
| Number: | 1. |
| Length: | 0.5 cm. |
| Style: | |
| Length: | 0.4 cm. |
| Color: | RHS Green 143C. |
| Stigma: | |
| Shape: | Round. |
| Color: | RHS Green-White 157A. |
| Ovary Color: | RHS Yellow-Green 144D. |

Other Characteristics

Seeds and fruits: 10 to 20 seeds per fruit.

We claim:

1. An *Impatiens hawkeri* plant designated 'NGT-15-5000', 'NGT-17-7039', 'NGT-18-7090', or 'NGT-18-3080', representative seed deposited at the NCIMB in Aberdeen, Scotland, accorded Accession numbers 43657, 43739, 43708 and 43709 respectively.

2. A plant or a plant part thereof produced by growing the plant of claim 1, wherein the plant or plant part comprises at least one cell of *Impatiens hawkeri* 'NGT-15-5000', 'NGT-17-7039', 'NGT-18-7090', or 'NGT-18-3080'.

3. An *Impatiens* plant or part thereof, having all of the physiological and morphological characteristics of the plant of claim 1.

4. A tissue or cell culture of regenerable cells produced from the plant of claim 1.

5. The tissue or cell culture of claim 4, comprising tissues or cells from a plant part selected from the group consisting of leaves, vegetative cuttings, pollen, embryos, cotyledons, hypocotyl, meristematic cells, roots, root tips, pistils, anthers, flowers and stems.

6. A method of producing *Impatiens* progeny comprising the steps of (a) crossing any of the plants *Impatiens hawkeri* 'NGT-15-5000', 'NGT-17-7039', 'NGT-18-7090', or 'NGT-18-3080', representative seed having been deposited at the NCIMB in Aberdeen, Scotland, accorded Accession numbers 43657, 43739, 43708 and 43709 respectively, as a female or male parent with another *Impatiens* plant, and (b) selecting progeny.

7. The method according to claim 6, wherein the second *Impatiens* plant is *hawkeri* 'NGT-15-5000', 'NGT-17-7039', 'NGT-18-7090', or 'NGT-18-3080', representative seed having been deposited at the NCIMB.

8. An *Impatiens hawkeri* seed that produces the *Impatiens hawkeri* plants of claim 1.

9. A method for developing an *Impatiens* plant in a plant breeding program using plant breeding techniques, including crossing, recurrent selection, mutation breeding, wherein said mutation breeding selects for a mutation that is spontaneously or naturally induced or artificially induced, backcrossing, pedigree breeding, marker enhanced selection, haploid/double haploid production or transformation to a plant of *Impatiens hawkeri* 'NGT-15-5000', 'NGT-17-7039', 'NGT-18-7090', or 'NGT-18-3080' representative seed having been deposited at the NCIMB in Aberdeen, Scotland, accorded Accession numbers 43657, 43739, 43708 and 43709 respectively or its parts, wherein application of said techniques results in development of an *Impatiens* plant.

* * * * *